(12) United States Patent
Motegi

(10) Patent No.: US 11,168,199 B2
(45) Date of Patent: Nov. 9, 2021

(54) POLYCARBONATE RESIN COMPOSITION

(71) Applicant: Mitsubishi Engineering-Plastics Corporation, Minato-ku (JP)

(72) Inventor: Atsushi Motegi, Hiratsuka (JP)

(73) Assignee: Mitsubishi Engineering-Plastics Corporation, Minato-ku (JP)

( * ) Notice: Subject to any disclaimer, the term of this patent is extended or adjusted under 35 U.S.C. 154(b) by 0 days.

(21) Appl. No.: 16/339,505

(22) PCT Filed: Sep. 4, 2017

(86) PCT No.: PCT/JP2017/031780
§ 371 (c)(1),
(2) Date: Apr. 4, 2019

(87) PCT Pub. No.: WO2018/096758
PCT Pub. Date: May 31, 2018

(65) Prior Publication Data
US 2019/0233616 A1    Aug. 1, 2019

(30) Foreign Application Priority Data

Nov. 28, 2016 (JP) .............................. JP2016-230074
Nov. 28, 2016 (JP) .............................. JP2016-230075
(Continued)

(51) Int. Cl.
*C08K 5/3475* (2006.01)
*C07D 405/10* (2006.01)
(Continued)

(52) U.S. Cl.
CPC .......... *C08K 5/3475* (2013.01); *C07D 405/10* (2013.01); *C08G 64/06* (2013.01);
(Continued)

(58) Field of Classification Search
CPC ........ C08K 5/3475; C08K 5/49; C08K 5/005; C08K 2201/014; C07D 405/10;
(Continued)

(56) References Cited

U.S. PATENT DOCUMENTS 5,952,096 A     9/1999 Yamashita et al.
2007/0155867 A1  7/2007 Ikari et al.
(Continued)

FOREIGN PATENT DOCUMENTS

EP    0 786 675 A2    7/1997
EP    2 287 655 A1    2/2011
(Continued)

OTHER PUBLICATIONS

International Search Report dated Nov. 21, 2017 in PCT/JP2017/031780 filed Sep. 4, 2017.
(Continued)

*Primary Examiner* — Ling Siu Choi
*Assistant Examiner* — Ronald Grinsted
(74) *Attorney, Agent, or Firm* — Oblon, McClelland, Maier & Neustadt, L.L.P.

(57) ABSTRACT

Provided is a polycarbonate resin composition that can block ultraviolet light as well as light on the visible light side therefrom at wavelengths of 400 to 420 nm, and that is free of the problem of gas generation during molding. The polycarbonate resin composition characteristically comprises, per 100 parts by mass of a polycarbonate resin (A), (i) 0.02 to 1 parts by mass of a sesamol group-containing benzotriazole ultraviolet absorber (B1) having a maximum absorption wavelength of at least 375 nm in the absorption curve determined according to JIS K 7105 using the following formula, or (ii) 0.08 to 1 parts by mass of a sesamol group-containing benzotriazole ultraviolet absorber (B2) having a maximum absorption wavelength of at least 360
(Continued)

nm and less than 375 nm in the absorption curve determined according to JIS K 7105 using the following formula; and 0.01 to 0.5% by mass of a stabilizer (C).

19 Claims, 1 Drawing Sheet

(30) Foreign Application Priority Data

| | | | |
|---|---|---|---|
| Jul. 25, 2017 | (JP) | ............................. | JP2017-143918 |
| Jul. 25, 2017 | (JP) | ............................. | JP2017-143919 |
| Aug. 16, 2017 | (JP) | ............................. | JP2017-157212 |
| Aug. 16, 2017 | (JP) | ............................. | JP2017-157213 |

(51) Int. Cl.
 *C08G 64/06* (2006.01)
 *C08K 5/49* (2006.01)
 *C08L 69/00* (2006.01)
 *G02B 1/04* (2006.01)
 *G02B 5/20* (2006.01)
 *C07D 405/04* (2006.01)
 *C08K 5/00* (2006.01)

(52) U.S. Cl.
 CPC ................ *C08K 5/49* (2013.01); *C08L 69/00* (2013.01); *G02B 1/04* (2013.01); *G02B 5/208* (2013.01); *C07D 405/04* (2013.01); *C08K 5/005* (2013.01); *C08K 2201/014* (2013.01); *G02B 1/041* (2013.01)

(58) Field of Classification Search
 CPC ....... C07D 405/04; C08G 64/06; C08L 69/00; G02B 1/04; G02B 5/208; G02B 1/041

USPC .......................................................... 252/589
 See application file for complete search history.

(56) References Cited

U.S. PATENT DOCUMENTS

| | | |
|---|---|---|
| 2012/0172497 A1 | 7/2012 | Chi et al. |
| 2014/0364546 A1 | 12/2014 | Okamoto et al. |

FOREIGN PATENT DOCUMENTS

| | | | |
|---|---|---|---|
| EP | 3 081 965 A1 | | 10/2016 |
| JP | 6-51840 B2 | | 6/1987 |
| JP | 0786675 | * | 1/1997 |
| JP | 9-263694 A | | 10/1997 |
| JP | 9-291205 A | | 11/1997 |
| JP | 2001-131399 A | | 5/2001 |
| JP | 2012-25680 A | | 2/2012 |
| JP | 2012025680 | * | 2/2012 |
| JP | 2012-41333 A | | 3/2012 |
| JP | 201241333 | * | 3/2012 |
| JP | 2013-107928 A | | 6/2013 |
| JP | 2013-139097 A | | 7/2013 |
| JP | 2014-151540 A | | 8/2014 |
| JP | 2015-189933 A | | 11/2015 |
| JP | 2015-196694 A | | 11/2015 |
| WO | WO 2005/069061 A1 | | 7/2005 |

OTHER PUBLICATIONS

Office Action dated Aug. 31, 2021, in Japanese Patent Application No. 2017-157212 (English translation only).

\* cited by examiner

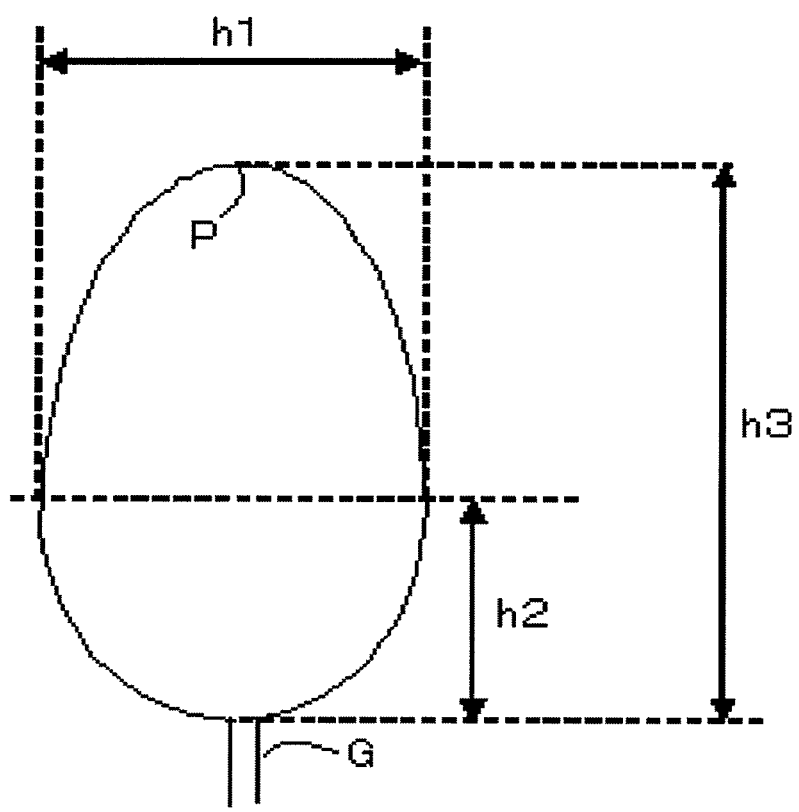

POLYCARBONATE RESIN COMPOSITION

TECHNICAL FIELD

The present invention relates to a polycarbonate resin composition and more particularly relates to a polycarbonate resin composition that can block light at wavelengths of 400 to 420 nm on the visible light side from ultraviolet light, and that is free of the problem of gas generation during molding.

BACKGROUND ART

The eyes are routinely exposed to damage from sunlight, and it is thus important to protect the eyes from ultraviolet light, the wavelength of which extends to 400 nm. In addition, recent research has shown that the wavelength band on the visible light side from ultraviolet light can also damage eye tissue and is a cause of, for example, cataracts. Moreover, as devices and lighting that employ LEDs as a light source have become more widespread, there have also been reports that blue light, which is present in large amounts in LED light sources, is a cause of eye disease.

There is thus demand for materials that block ultraviolet light as well as light at wavelengths of 400 to 420 nm, which is on the visible light side therefrom.

Polycarbonate resins generally exhibit excellent mechanical properties, weathering resistance, and transparency, and polycarbonate resin compositions that incorporate an ultraviolet absorber are used as ultraviolet-absorbing transparent materials for, e.g., eyeglasses, sunglasses, goggles, various lighting covers, and so forth. For example, benzophenones, benzotriazoles, triazines, salicylates, and so forth are used as the ultraviolet absorber (for example, PTL 1 and PTL 2).

However, a practical polycarbonate resin composition that can effectively absorb and block the 400 to 420 nm wavelengths is not known.

In addition, when blocking light with a wavelength of 420 nm has been pursued using conventional ultraviolet absorbers such as those indicated above, a problem has been that their large levels of incorporation have ended up causing a large amount of gas generation during molding.

Resin compositions comprising a polycarbonate resin and such ultraviolet absorbers are known, but at present a polycarbonate resin composition that can effectively absorb and block the 400 to 420 nm wavelengths while being free of the problem of gas generation during molding is not known.

CITATION LIST

Patent Literature

[PTL 1] JP H09-291205 A
[PTL 2] JP H06-51840 B

SUMMARY OF INVENTION

Technical Problem

The present invention was pursued considering the circumstances described above and has as an object (problem) the provision of a polycarbonate resin composition that can block ultraviolet light as well as light on the visible light side therefrom at wavelengths of 400 to 420 nm, and that is free of the problem of gas generation during molding.

Solution to Problem

As a result of extensive and intensive investigations in order to address the aforementioned problem, the present inventor discovered that, through the incorporation, in prescribed amounts in each case, of an ultraviolet absorber having a prescribed maximum absorption wavelength and a phosphorus stabilizer, a polycarbonate resin composition is obtained that can block light at wavelengths of 400 to 420 nm and that is free of the problem of gas generation during molding.

The present invention relates to a polycarbonate resin composition comprising, per 100 parts by mass of a polycarbonate resin (A), (i) 0.02 to 1 parts by mass of a sesamol group-containing benzotriazole ultraviolet absorber (B1) having a maximum absorption wavelength of at least 375 nm in the absorption curve determined according to JIS K 7105 using the following formula, or (ii) 0.08 to 1 parts by mass of a sesamol group-containing benzotriazole ultraviolet absorber (B2) having a maximum absorption wavelength of at least 360 nm and less than 375 nm in the absorption curve determined according to JIS K 7105 using the following formula; and 0.01 to 0.5 parts by mass of a stabilizer (C).

[absorbance of the polycarbonate resin that contains 0.005% by mass of the ultraviolet absorber]–
[absorbance of only the polycarbonate resin]

Advantageous Effects of Invention

The polycarbonate resin composition according to the present invention can block ultraviolet light as well as light on the visible light side therefrom at wavelengths of 400 to 420 nm, and is free of the problem of gas generation during molding.

BRIEF DESCRIPTION OF DRAWINGS

FIG. 1 is a plan view of a drop-shaped mold used in the evaluation of mold contamination in the examples.

DESCRIPTION OF EMBODIMENTS

The present invention is described in detail in the following using embodiments, examples, and so forth.

Unless specifically indicated otherwise, in this Description the specification of a numerical value range is used in the sense of including the numerical values before and after the "to" that are used as the lower limit and upper limit.

The present invention is as described above and is constituted of a first invention, which incorporates (i) 0.02 to 1 parts by mass of a sesamol group-containing benzotriazole ultraviolet absorber (B1) having a maximum absorption wavelength of at least 375 nm, and a second invention, which incorporates (ii) 0.08 to 1 parts by mass of a sesamol group-containing benzotriazole ultraviolet absorber (B2) having a maximum absorption wavelength of at least 360 nm and less than 375 nm in the absorption curve determined according to JIS K 7105 using the following formula.

The aforementioned first invention is described first hereinbelow, followed by a description of the aforementioned second invention.

First Invention

The first invention is described first in the following.

The first invention relates to the polycarbonate resin composition and molded article described in the following.

[1] A polycarbonate resin composition comprising, per 100 parts by mass of a polycarbonate resin (A), 0.02 to 1 parts by mass of an ultraviolet absorber (B1) having a maximum absorption wavelength of at least 375 nm in the absorption curve determined according to JIS K 7105 using the following formula, and 0.01 to 0.5 parts by mass of a stabilizer (C).

[absorbance of the polycarbonate resin that contains 0.005% by mass of the ultraviolet absorber]−
[absorbance of only the polycarbonate resin]

[2] The polycarbonate resin composition according to [1], wherein the ultraviolet absorber (B1) is a sesamol group-containing benzotriazole ultraviolet absorber.

[3] The polycarbonate resin composition according to [1] or [2], wherein the ultraviolet absorber (B1) is an ultraviolet absorber represented by the following general formula (1).

[C1]

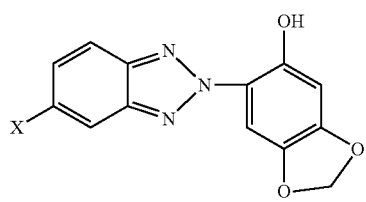

(1)

(In the formula, X represents a halogen atom.)

[4] The polycarbonate resin composition according to any of [1] to [3], that further contains, per 100 parts by mass of the polycarbonate resin (A), at least 0.01 parts by mass and less than 0.08 parts by mass of the sesamol group-containing benzotriazole ultraviolet absorber (B2) having a maximum absorption wavelength of at least 360 nm and less than 375 nm in the absorption curve determined according to JIS K 7105 using the formula given above.

[5] The polycarbonate resin composition according to any of [1] to [4], that further contains, per 100 parts by mass of the polycarbonate resin (A), 0.01 to 0.2 parts by mass of an ultraviolet absorber (B2) having a maximum absorption wavelength of less than 360 nm in the absorption curve determined according to JIS K 7105 using the formula given above.

[6] The polycarbonate resin composition according to [5], wherein the ultraviolet absorber (B2) is at least one selection from benzotriazole ultraviolet absorbers lacking sesamol group, triazine ultraviolet absorbers, malonate ester ultraviolet absorbers, and benzoxazine ultraviolet absorbers.

[7] The polycarbonate resin composition according to any of [1] to [6], wherein the transmittance measured according to JIS K 7105 at a wavelength of 420 nm on a 2 mm-thick molded article is not greater than 25%.

[8] A molded article of the polycarbonate resin composition according to any of [1] to [7].

The components and so forth constituting the polycarbonate resin composition of the first invention are described in detail in the following.

[Polycarbonate Resin (A)]

The polycarbonate resin is a polymer with a basic structure that has the carbonate bond given by the formula —[—O—X—O—C(=O)—]—. X in the formula is generally a hydrocarbon, but an X incorporating a heteroatom or hetero bond may be used in order to impart various properties.

Polycarbonate resins can be classified into aromatic polycarbonate resins, in which each of the carbon atoms directly bonded to the carbonate bond is an aromatic carbon, and aliphatic polycarbonate resins, in which they are aliphatic carbon atoms, and either of these can be used. Aromatic polycarbonate resins are preferred therebetween considering, for example, the heat resistance, mechanical properties, and electrical properties.

There are no limitations on the specific species of polycarbonate resin, and examples here are polycarbonate polymers provided by the reaction of a dihydroxy compound with a carbonate precursor. A polyhydroxy compound and so forth may also be reacted here in addition to the dihydroxy compound and carbonate precursor. A method may also be used in which carbon dioxide is reacted as the carbonate precursor with a cyclic ether. The polycarbonate polymer may be a linear or branched chain. In addition, the polycarbonate polymer may be a homopolymer composed of a single species of repeat unit or may be a copolymer having two or more species of repeat units. Various copolymerization modes may be selected for such a copolymer, e.g., random copolymer, block copolymer, and so forth. A polycarbonate polymer as described here is generally a thermoplastic resin.

Among the monomers comprising the starting materials for aromatic polycarbonate resins, aromatic dihydroxy compounds can be exemplified by the following:

dihydroxybenzenes, e.g., 1,2-dihydroxybenzene, 1,3-dihydroxybenzene (i.e., resorcinol), and 1,4-dihydroxybenzene;

dihydroxybiphenyls, e.g., 2,5-dihydroxybiphenyl, 2,2'-dihydroxybiphenyl, and 4,4'-dihydroxybiphenyl;

dihydroxynaphthalenes, e.g., 2,2'-dihydroxy-1,1'-binaphthyl, 1,2-dihydroxynaphthalene, 1,3-dihydroxynaphthalene, 2,3-dihydroxynaphthalene, 1,6-dihydroxynaphthalene, 2,6-dihydroxynaphthalene, 1,7-dihydroxynaphthalene, and 2,7-dihydroxynaphthalene;

dihydroxydiaryl ethers such as 2,2'-dihydroxydiphenyl ether, 3,3'-dihydroxydiphenyl ether, 4,4'-dihydroxydiphenyl ether, 4,4'-dihydroxy-3,3'-dimethyldiphenyl ether, 1,4-bis(3-hydroxyphenoxy)benzene, and 1,3-bis(4-hydroxyphenoxy)benzene;

bis(hydroxyaryl)alkanes such as 2,2-bis(4-hydroxyphenyl)propane (i.e., bisphenol A), 1,1-bis(4-hydroxyphenyl)propane, 2,2-bis(3-methyl-4-hydroxyphenyl)propane, 2,2-bis(3-methoxy-4-hydroxyphenyl)propane, 2-(4-hydroxyphenyl)-2-(3-methoxy-4-hydroxyphenyl)propane, 1,1-bis(3-tert-butyl-4-hydroxyphenyl)propane, 2,2-bis(3,5-dimethyl-4-hydroxyphenyl)propane, 2,2-bis(3-cyclohexyl-4-hydroxyphenyl)propane, 2-(4-hydroxyphenyl)-2-(3-cyclohexyl-4-hydroxyphenyl)propane, α,α'-bis(4-hydroxyphenyl)-1,4-diisopropylbenzene, 1,3-bis[2-(4-hydroxyphenyl)-2-propyl]benzene, bis(4-hydroxyphenyl)methane, bis(4-hydroxyphenyl)cyclohexylmethane, bis(4-hydroxyphenyl)phenylmethane, bis(4-hydroxyphenyl)(4-propenylphenyl)methane, bis(4-hydroxyphenyl)diphenylmethane, bis(4-hydroxyphenyl)naphthylmethane, 1,1-bis(4-hydroxyphenyl)ethane, 1,1-bis(4-hydroxyphenyl)-1-phenylethane, 1,1-bis(4-hydroxyphenyl)-1-naphthylethane, 1,1-bis(4-hydroxyphenyl)butane, 2,2-bis(4-hydroxyphenyl)butane, 2,2-bis(4-hydroxyphenyl)pentane, 1,1-bis(4-hydroxyphenyl)hexane, 2,2-bis(4-hydroxyphenyl)hexane, 1,1-bis(4-hydroxyphenyl)octane, 2,2-bis(4-hydroxyphenyl)octane, 4,4-bis(4-hydroxyphenyl)heptane, 2,2-bis(4-hydroxyphenyl)nonane, 1,1-bis(4-hydroxyphenyl)decane, and 1,1-bis(4-hydroxyphenyl)dodecane;

bis(hydroxyaryl)cycloalkanes such as 1,1-bis(4-hydroxyphenyl)cyclopentane, 1,1-bis(4-hydroxyphenyl)cyclohexane, 1,1-bis(4-hydroxyphenyl)-3,3-dimethylcyclohexane, 1,1-bis(4-hydroxyphenyl)-3,4-dimethylcyclohexane, 1,1-bis(4-hydroxyphenyl)-3,5-dimethylcyclohexane, 1,1-bis(4-hydroxyphenyl)-3,3,5-trimethylcyclohexane, 1,1-bis(4-hydroxy-3,5-dimethylphenyl)-3,3,5-trimethylcyclohexane, 1,1-bis(4-hydroxyphenyl)-3-propyl-5-methylcyclohexane, 1,1-bis(4-hydroxyphenyl)-3-tert-butylcyclohexane, 1,1-bis(4-hydroxyphenyl)-4-tert-butylcyclohexane, 1,1-bis(4-hydroxyphenyl)-3-phenylcyclohexane, and 1,1-bis(4-hydroxyphenyl)-4-phenylcyclohexane;

cardo structure-containing bisphenols such as 9,9-bis(4-hydroxyphenyl)fluorene and 9,9-bis(4-hydroxy-3-methylphenyl)fluorene;

dihydroxydiaryl sulfides such as 4,4'-dihydroxydiphenyl sulfide and 4,4'-dihydroxy-3,3'-dimethyldiphenyl sulfide;

dihydroxydiaryl sulfoxides such as 4,4'-dihydroxydiphenyl sulfoxide and 4,4'-dihydroxy-3,3'-dimethyldiphenyl sulfoxide; and dihydroxydiaryl sulfones such as 4,4'-dihydroxydiphenyl sulfone and 4,4'-dihydroxy-3,3'-dimethyldiphenyl sulfone.

Among the preceding, the bis(hydroxyaryl)alkanes are preferred and among them the bis(4-hydroxyphenyl)alkanes are preferred, while 2,2-bis(4-hydroxyphenyl)propane (i.e., bisphenol A) is particularly preferred from the standpoints of the impact resistance and heat resistance.

A single aromatic dihydroxy compound may be used or any combination of two or more in any proportions may be used.

The monomers comprising the starting materials for aliphatic polycarbonate resins can be exemplified by the following:

alkanediols such as ethane-1,2-diol, propane-1,2-diol, propane-1,3-diol, 2,2-dimethylpropane-1,3-diol, 2-methyl-2-propylpropane-1,3-diol, butane-1,4-diol, pentane-1,5-diol, hexane-1,6-diol, and decane-1,10-diol;

cycloalkanediols such as cyclopentane-1,2-diol, cyclohexane-1,2-diol, cyclohexane-1,4-diol, 1,4-cyclohexanedimethanol, 4-(2-hydroxyethyl)cyclohexanol, and 2,2,4,4-tetramethylcyclobutane-1,3-diol;

glycols such as ethylene glycol, 2,2'-oxydiethanol (i.e., diethylene glycol), triethylene glycol, propylene glycol, and spiroglycol;

aralkyl diols such as 1,2-benzenedimethanol, 1,3-benzenedimethanol, 1,4-benzenedimethanol, 1,4-benzenediethanol, 1,3-bis(2-hydroxyethoxy)benzene, 1,4-bis(2-hydroxyethoxy)benzene, 2,3-bis(hydroxymethyl)naphthalene, 1,6-bis(hydroxyethoxy)naphthalene, 4,4'-biphenyldimethanol, 4,4'-biphenyldiethanol, 1,4-bis(2-hydroxyethoxy)biphenyl, bisphenol A bis(2-hydroxyethyl) ether, and bisphenol S bis(2-hydroxyethyl) ether; and cyclic ethers such as 1,2-epoxyethane (i.e., ethylene oxide), 1,2-epoxypropane (i.e., propylene oxide), 1,2-epoxycyclopentane, 1,2-epoxycyclohexane, 1,4-epoxycyclohexane, 1-methyl-1,2-epoxycyclohexane, 2,3-epoxynorbornane, and 1,3-epoxypropane.

Of the monomers comprising the starting materials for polycarbonate resins, the carbonate precursor can be exemplified by carbonyl halides and carbonate esters. A single carbonate precursor may be used or any combination of two or more in any proportions may be used.

The carbonyl halides can be specifically exemplified by phosgene and by haloformates such as the bischloroformates of dihydroxy compounds and the monochloroformates of dihydroxy compounds.

The carbonate esters can be specifically exemplified by diaryl carbonates such as diphenyl carbonate and ditolyl carbonate; dialkyl carbonates such as dimethyl carbonate and diethyl carbonate; and carbonates of dihydroxy compounds, e.g., biscarbonates of dihydroxy compounds, monocarbonates of dihydroxy compounds, and cyclic carbonates.

There are no particular limitations on the method of producing the polycarbonate resin, and any method can be used. Examples thereof are the interfacial polymerization method, melt transesterification method, pyridine method, ring-opening polymerization of a cyclic carbonate compound, and solid-state transesterification of a prepolymer.

The molecular weight of the polycarbonate resin (A), expressed as the viscosity-average molecular weight (Mv), is preferably in the range from 16,000 to 50,000 and is more preferably at least 18,000 and still more preferably at least 20,000 and is more preferably not more than 45,000, still more preferably not more than 40,000, and particularly preferably not more than 38,000. A viscosity-average molecular weight of less than 16,000 facilitates a decline in the impact resistance of the molded article and creates a cracking risk and is thus disfavored. A viscosity-average molecular weight of greater than 50,000 results in a poor flowability and facilitates the appearance of problems with the moldability and is thus also disfavored.

A mixture of two or more polycarbonate resins having different viscosity-average molecular weights may be used for the polycarbonate resin (A), in which case a polycarbonate resin having a viscosity-average molecular weight outside the aforementioned preferred range may be admixed.

In the present invention, the viscosity-average molecular weight [Mv] of the polycarbonate resin refers to the value calculated using Schnell's viscosity equation, i.e., $\eta = 1.23 \times 10^{-4} Mv^{0.83}$, wherein the intrinsic viscosity [$\eta$] (unit: dl/g) is determined at a temperature of 20° C. using methylene chloride as the solvent and using a Ubbelohde viscometer. The intrinsic viscosity [$\eta$] is the value calculated using the following formula and the specific viscosity [$\eta_{sp}$] measured at each solution concentration [C] (g/dl).

$$\eta = \lim_{c \to 0} \eta_{sp}/c \qquad \text{[Math. 1]}$$

In addition, a combination of polycarbonate resin with another thermoplastic resin may be used in the present invention. Moreover, it may be structured as a copolymer in which polycarbonate resin is the major portion, for example, as a copolymer of a polycarbonate resin with a siloxane structure-containing oligomer or polymer, with the goal of raising the flame retardancy and impact resistance still further; as a copolymer of a polycarbonate resin with a phosphorus atom-containing monomer, oligomer, or polymer, with the goal of raising the thermal oxidation stability and flame retardancy still further; as a copolymer of a polycarbonate resin with a dihydroxyanthraquinone structure-containing monomer, oligomer, or polymer, with the goal of improving the thermal oxidation stability; as a copolymer of a polycarbonate resin with an oligomer or polymer having an olefinic structure, e.g., polystyrene, in order to improve the optical properties; or as a copolymer of a polycarbonate resin with a polyester resin oligomer or polymer with the goal of enhancing the chemical resistance.

In addition, the polycarbonate resin may contain a polycarbonate oligomer in order to bring about an improved appearance for the molded article and improve the flowability. The viscosity-average molecular weight (Mv) of this polycarbonate oligomer is generally at least 1,500 and is preferably at least 2,000 and is generally not more than 9,500 and is preferably not more than 9,000. The incorporated polycarbonate oligomer is preferably not more than 30% by mass of the polycarbonate resin (including the polycarbonate oligomer).

The polycarbonate resin may be a virgin starting material, but may also be a polycarbonate resin that has been regenerated from post-consumer products (also known as material recycled polycarbonate resin).

However, regenerated polycarbonate resin preferably is not more than 80% by mass and more preferably not more than 50% by mass of the polycarbonate resin. Since regenerated polycarbonate resin has a high potential for deterioration, e.g., thermal deterioration, ageing deterioration, and so forth, the use of such a polycarbonate resin in amounts larger than the indicated range creates the possibility of causing a decline in the color and mechanical properties.

[Ultraviolet Absorber (B1)]

The polycarbonate resin composition according to the first invention contains an ultraviolet absorber (B1) for which the maximum absorption wavelength determined according to JIS K 7105 using the following formula (1) is at least 375 nm.

[absorbance of the polycarbonate resin that contains 0.005% by mass of the ultraviolet absorber]– [absorbance of only the polycarbonate resin]    (1)

The maximum absorption wavelength of the ultraviolet absorber (B1) is defined in the present invention as the maximum absorption wavelength in the absorption curve obtained in accordance with formula (1) by subtracting, from the absorbance of a flat plate-shaped molded article of the polycarbonate resin containing 0.005% by mass of the ultraviolet absorber, the absorbance of a flat plate-shaped molded article with the same shape and same thickness of the same polycarbonate resin not containing the ultraviolet absorber. It is thought that in principle the thusly defined maximum absorption wavelength will not vary as a function of the thickness of the flat plate-shaped test specimen used, but the comparison is preferably carried out in the present invention at a thickness of 2 mm.

The same definition also applies to the maximum absorption wavelength for the ultraviolet absorbers (B2) and (B3) described below.

The specific conditions in the method for measuring and determining the maximum absorption wavelength are as described in the examples.

While the maximum absorption wavelength of the ultraviolet absorber (B1) is at least 375 nm, the upper limit parts by mass, the transmittance of the resulting resin composition in the 400 to 420 nm wavelength region is then too high. When this content exceeds 1 parts by mass, the transmittance in the 400 to 420 nm wavelength region is low, but gas generation during molding becomes substantial and the volatile fraction adheres to the molded article and the appearance of the product is then substantially impaired. The content of the ultraviolet absorber (B1) per 100 parts by mass of the polycarbonate resin (A) is preferably at least 0.025 parts by mass and not more than 0.8 parts by mass, more preferably not more than 0.7 parts by mass, and still more preferably not more than 0.6 parts by mass.

[Ultraviolet Absorber (B2)]

The polycarbonate resin composition according to the present invention preferably additionally contains a sesamol group-containing benzotriazole ultraviolet absorber (B2) having a maximum absorption wavelength of at least 360 nm and less than 375 nm in the absorption curve determined according to JIS K 7105 from formula (1).

The incorporation of the ultraviolet absorber (B2) makes it possible to ameliorate the trend wherein the transmittance around 320 nm is prone to increase when the content of the ultraviolet absorber (B1) is relatively small.

The ultraviolet absorber represented by the following general formula (2) is preferred for the sesamol group-containing benzotriazole ultraviolet absorber (B2) on this maximum absorption wavelength is preferably not more than 420 nm and is more preferably not more than 400 nm.

While this ultraviolet absorber (B1) may be selected from, for example, benzotriazole compounds, benzophenone compounds, triazine compounds, benzoate compounds, phenyl salicylate ester compounds, cyanoacrylate compounds, malonate ester compounds, and oxalic acid anilides that in each case have a maximum absorption wavelength of at least 375 nm, benzotriazole ultraviolet absorbers are preferred, sesamol group (the benzo[1,3]dioxol-5-ol group)-containing benzotriazole ultraviolet absorbers are more preferred, and the ultraviolet absorber represented by the following general formula (1) is particularly preferred.

[C2]

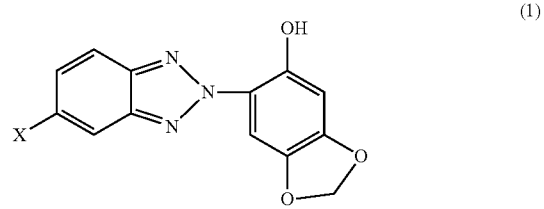

(1)

The X in general formula (1) is a halogen atom and preferably is a halogen atom such as chlorine, bromine, fluorine, or iodine and is more preferably a chlorine atom, and 6-(5-chloro-2H-benzotriazol-2-yl)benzo[1,3]dioxol-5-ol is thus specifically preferred.

The content of the ultraviolet absorber (B1) is 0.02 to 1 parts by mass per 100 parts by mass of the polycarbonate resin (A). When this content is less than 0.02 having a maximum absorption wavelength of at least 360 nm and less than 375 nm in the absorption curve determined according to JIS K 7105 from formula (1).

[C3]

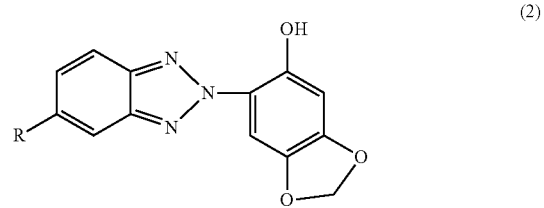

(2)

(In general formula (2), R represents a hydrogen atom, alkyl group having 1 to 8 carbon atoms, alkoxy group having 1 to 8 carbon atoms, hydroxyl group, carboxyl group, alkyloxycarbonyl group having 1 to 8 carbon atoms in the alkyl group, hydroxyalkyl group having 1 to 8 carbon atoms, or alkylcarbonyloxyalkyl group having 1 to 8 carbon atoms in each of the alkyl groups.)

The R in general formula (2) can be specifically exemplified by the following: a hydrogen atom; optionally substituted linear or branched alkyl groups having 1 to 8 carbon atoms, e.g., methyl group, ethyl group, propyl group, isopropyl group, n-butyl group, isobutyl group, sec-butyl group, tert-butyl group, n-hexyl group, n-octyl group, and 2-ethylhexyl group; optionally substituted linear or branched alkoxy groups having 1 to 8 carbon atoms, e.g., methoxy group, ethoxy group, propoxy group, isopropoxy group, n-butoxy group, isobutoxy group, sec-butoxy group, tert-butoxy group, n-hexyloxy group, n-octyloxy group, and 2-ethylhexyloxy group; hydroxyl group; carboxyl group; optionally substituted linear or branched alkyloxycarbonyl groups having 1 to 8 carbon atoms in the alkyl group, e.g., methoxycarbonyl group, ethoxycarbonyl group, isopropoxycarbonyl group, n-butoxycarbonyl group, isobutyoxycarbonyl group, sec-butoxycarbonyl group, tert-butoxycarbonyl group, n-hexyloxycarbonyl group, n-octyloxycarbonyl group, and 2-ethylhexyloxycarbonyl group; optionally substituted linear or branched hydroxyalkyl groups having 1 to 8 carbon atoms, e.g., hydroxymethyl group, hydroxyethyl group, hydroxypropyl group, hydroxybutyl group, hydroxyhexyl group, and hydroxyoctyl group; and optionally substituted linear or branched alkylcarbonyloxyalkyl groups in which each alkyl has 1 to 8 carbon atoms, e.g., methylcarbonyloxymethyl group, ethylcarbonyloxymethyl group, propylcarbonyloxymethyl group, butylcarbonyloxymethyl group, hexylcarbonyloxymethyl group, heptylcarbonyloxymethyl group, octylcarbonyloxymethyl group, methylcarbonyloxyethyl group, ethylcarbonyloxyethyl group, propylcarbonyloxyethyl group, butylcarbonyloxyethyl group, hexylcarbonyloxyethyl group, heptylcarbonyloxyethyl group, and octylcarbonyloxyethyl group.

Preferred among the preceding for R are the hydrogen atom, alkyl groups, alkoxy groups, hydroxyl group, carboxyl group, alkyloxycarbonyl groups, hydroxyalkyl groups, and alkylcarbonyloxyalkyl groups. More preferred are hydrogen atom, methyl group, methoxy group, n-octyloxy group, hydroxyl group, carboxyl group, methoxycarbonyl group, n-octyloxycarbonyl group, hydroxyethyl group, methylcarbonyloxyethyl group, and heptylcarbonyloxyethyl group.

The following are preferred examples of compounds represented by general formula (2) and having a maximum absorption wavelength of at least 360 nm and less than 375 nm: 6-(2H-benzotriazol-2-yl)benzo[1,3]dioxol-5-ol, 6-(5-n-heptylcarbonyloxyethyl -2H-benzotriazol-2-yl)benzo[1,3]dioxol-5-ol, 6-(5-isoheptylcarbonyloxyethyl-2H-benzotriazol-2-yl)benzo[1,3]dioxol-5-ol, 6-(5-methyl-2H-benzotriazol-2-yl)benzo[1,3]dioxol-5-ol, 6-(5-methoxy-2H-benzotriazol-2-yl)benzo[1,3]dioxol-5-ol, 6-(5-hydroxy-2H-benzotriazol-2-yl)benzo[1,3]dioxol-5-ol, 6-(5-octyloxy-2H-benzotriazol-2-yl)benzo[1,3]dioxol-5-ol, 6-(5-carboxy-2H-benzotriazol-2-yl)benzo[1,3]dioxol-5-ol, 6-(5-hydroxyethyl-2H-benzotriazol-2-yl)benzo[1,3]dioxol-5-ol, and 6-(5-methylcarbonyloxyethyl-2H-benzotriazol-2-yl)benzo[1,3]dioxol-5-ol.

Particularly preferred among the preceding are 6-(2H-benzotriazol-2-yl)benzo[1,3]dioxol-5-ol, 6-(5-n-heptylcarbonyloxyethyl -2H-benzotriazol-2-yl)benzo[1,3]dioxol-5-ol, and 6-(5-isoheptylcarbonyloxyethyl-2H-benzotriazol-2-yl)benzo[1,3]dioxol-5-ol.

The preferred content of the ultraviolet absorber (B2) is from at least 0.01 parts by mass to less than 0.08 parts by mass per 100 parts by mass of the polycarbonate resin (A). Transmission around the 320 nm wavelength by the resulting resin composition readily occurs at less than 0.01 parts by mass. While at and above 0.08 parts by mass, the occurrence of gas generation during molding is facilitated and the product appearance is readily impaired. The content of the ultraviolet absorber (B2) per 100 parts by mass of the polycarbonate resin (A) is more preferably at least 0.02 parts by mass and still more preferably at least 0.03 parts by mass and is more preferably not more than 0.07 parts by mass, still more preferably not more than 0.05 parts by mass, and particularly preferably not more than 0.04 parts by mass.

[Ultraviolet Absorber (B3)]

The polycarbonate resin composition according to the first invention preferably additionally contains (B3) an ultraviolet absorber having a maximum absorption wavelength of less than 360 nm in the absorption curve determined according to JIS K 7105 from formula (1).

The incorporation of the ultraviolet absorber (B3) makes it possible to ameliorate the trend wherein the transmittance around 320 nm is prone to increase when the content of the ultraviolet absorber (B1) is relatively small.

The ultraviolet absorber (B3) can be exemplified by benzotriazole compounds, benzophenone compounds, triazine compounds, benzoxazine compounds, benzoate compounds, phenyl salicylate ester compounds, cyanoacrylate compounds, malonate ester compounds, and oxalic acid anilides. Preferred among the preceding are benzotriazole compounds, triazine compounds, malonate ester compounds, and benzoxazine compounds. A single one of these may be used or two or more may be used.

The hydroxybenzophenone compounds can be exemplified by 2-hydroxy-4-octoxybenzophenone.

The malonate ester compounds can be exemplified by dimethyl (p-methoxybenzylidene)malonate, 2-(1-arylalkylidene)malonate esters, and tetraethyl 2,2'-(1,4-phenylenedimethylidene)bismalonate.

The triazine compounds can be exemplified by 2-(4,6-diphenyl-1,3,5-triazin-2-yl)-5-[(hexyl)oxy]phenol.

The benzoate compounds can be exemplified by 2,4-di-t-butylphenyl-3,5-di-t-butyl-4-hydroxybenzoate.

The benzoxazine compounds can be exemplified by 2,2'-(1,4-phenylene)bis(4H-3,1-benzoxazin-4-one).

The ultraviolet absorber (B3) is more preferably a benzotriazole ultraviolet absorber and is particularly preferably a benzotriazole compound that does not have a sesamol group. The following are preferred specific examples of such benzotriazole compounds: 2-(2-hydroxy-5-t-octylphenyl) -2H-benzotriazole, 2-(3-t-butyl-2-hydroxy-5-methylphenyl) -5-chloro-2H-benzotriazole, 2-[5-chloro(2H)-benzotriazol -2-yl]-4-methyl-6-(t-butyl)phenol, 2,4-di-tert-butyl -6-(5-chlorobenzotriazol-2-yl)phenol, (2-[5-chloro(2H)-benzotriazol -2-yl]-4,6-di(tert-pentyl)phenol), 3-[3-tert-butyl -5-(5-chloro-2H-benzotriazol-2-yl)-4-hydroxyphenyl]octyl propionate, 2-(3-t-butyl-5-methyl-2-hydroxyphenyl)-5-chlorobenzotriazole, 2-(2H-benzotriazol-2-yl)-6-dodecyl-4-methylphenol, 2-(2H-benzotriazol-2-yl)-p-cresol, 2-[(2H)-benzotriazol -2-yl]-4,6-bis(1-methyl-1-phenylethyl)phenol.

The preferred content of the ultraviolet absorber (B3) is 0.01 to 0.2 parts by mass per 100 parts by mass of the polycarbonate resin (A). Transmission around the 320 nm wavelength by the resulting resin composition readily occurs at less than 0.01 parts by mass. While at above 0.2 parts by mass, the occurrence of gas generation during molding is facilitated and the product appearance is readily impaired. The content of the ultraviolet absorber (B3) per 100 parts by mass of the polycarbonate resin (A) is more preferably at least 0.02 parts by mass and still more preferably at least 0.03 parts by mass and is more preferably not more than 0.15 parts by mass.

[Stabilizer (C)]

The polycarbonate resin composition according to the first invention contains a stabilizer (C). This stabilizer (C) is exemplified by phosphorus stabilizers, phenolic stabilizers, sulfur stabilizers, and so forth. The polycarbonate resin composition according to the second invention also contains a stabilizer (C), and its type, content, and so forth are the same as for the first invention. The description that follows also applies to the stabilizer (C) in the second invention.

[Phosphorus Stabilizer]

Through the incorporation of a phosphorus stabilizer in the polycarbonate resin composition according to the present invention, the polycarbonate resin composition assumes a good color and exhibits additional improvements in its resistance to thermal discoloration.

Any known phosphorus stabilizer can be used as the phosphorus stabilizer here. Specific examples are the oxo acids of phosphorus, e.g., phosphoric acid, phosphonic acid, phosphorous acid, phosphinic acid, and polyphosphoric acid; acidic pyrophosphate metal salts, e.g., sodium acidic pyrophosphate, potassium acidic pyrophosphate, and calcium acidic pyrophosphate; salts of phosphoric acid with a Group 1 or Group 2B metal, e.g., potassium phosphate, sodium phosphate, cesium phosphate, and zinc phosphate; phosphate compounds; phosphite compounds; and phosphonite compounds, with phosphite compounds being particularly preferred. By selecting a phosphite compound, a polycarbonate resin composition can be obtained that exhibits a higher resistance to discoloration and a better continuous production capability.

This phosphite compound is a trivalent phosphorus compound represented by the general formula $P(OR)_3$ where R represents a monovalent or divalent organic group.

This phosphite compound is exemplified by triphenyl phosphite, tris(monononylphenyl) phosphite, tris(monononyl/dinonyl-phenyl) phosphite, tris(2,4-di-tert-butylphenyl) phosphite, monooctyl diphenyl phosphite, dioctyl monophenyl phosphite, monodecyl diphenyl phosphite, didecyl monophenyl phosphite, tridecyl phosphite, trilauryl phosphite, tristearyl phosphite, distearyl pentaerythritol diphosphite, bis(2,4-di-tert-butyl-4-methylphenyl) pentaerythritol phosphite, bis(2,6-di-tert-butylphenyl) octyl phosphite, 2,2-methylenebis(4,6-di-tert-butylphenyl) octyl phosphite, tetrakis(2,4-di-tert-butylphenyl)-4,4'-biphenylene diphosphite, and 6-[3-(3-tert-butyl-hydroxy-5-methylphenyl)propoxy]-2,4,8,10-tetra-tert-butyldibenzo[d,f][1,3,2]dioxaphosphepine.

Among these phosphite compounds, the aromatic phosphite compounds represented by the following general formulas (3) and (4) are more preferred because they effectively increase the resistance to thermal discoloration exhibited by the polycarbonate resin composition according to the present invention.

[C4]

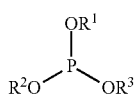

(3)

(In the formula, $R^1$, $R^2$, and $R^3$ each independently represent an aryl group having 6 to 30 carbon atoms.)

[C5]

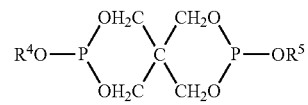

(4)

(In the formula, $R^4$ and $R^5$ each independently represent an aryl group having 6 to 30 carbon atoms.)

Among the phosphite compounds represented by formula (3), triphenyl phosphite, tris(monononylphenyl) phosphite, tris(2,4-di-tert-butylphenyl) phosphite, and so forth are preferred whereamong tris(2,4-di-tert-butylphenyl) phosphite is more preferred.

Among the phosphite compounds represented by formula (4), those having a pentaerythritol diphosphite structure, such as bis(2,4-di-tert-butyl-4-methylphenyl) pentaerythritol diphosphite, bis(2,6-di-tert-butyl-4-methylphenyl) pentaerythritol diphosphite, and bis(2,4-dicumylphenyl) pentaerythritol diphosphite, are particularly preferred.

Among the phosphite compounds, aromatic phosphite compounds with formula (4) provide an even better color and are thus more preferred.

A single phosphorus stabilizer may be incorporated or any combination of two or more phosphorus stabilizers in any proportions may be incorporated.

The content of the phosphorus stabilizer, per 100 parts by mass of the polycarbonate resin (A), is 0.01 to 0.5 parts by mass and preferably at least 0.02 parts by mass and more preferably at least 0.03 parts by mass, and is preferably not more than 0.4 parts by mass, more preferably not more than 0.3 parts by mass, and still more preferably not more than 0.2 parts by mass. The color and thermal discoloration resistance are unsatisfactory when the phosphorus stabilizer content is less than 0.005 parts by mass. At above 0.5 parts by mass, the thermal discoloration resistance actually deteriorates instead and the moist heat stability declines as well.

[Phenolic Stabilizer]

The polycarbonate resin composition according to the present invention may contain a phenolic stabilizer as the stabilizer. Hindered phenolic oxidation inhibitors are examples of phenolic stabilizers. Specific examples thereof are pentaerythritol tetrakis[3-(3,5-di-tert-butyl-4-hydroxyphenyl)propionate], octadecyl 3-(3,5-di-tert-butyl-4-hydroxyphenyl)propionate, thiodiethylenebis[3-(3,5-di-tert-butyl -4-hydroxyphenyl)propionate], N,N'-hexan-1,6-diylbis[3-(3,5-di-tert-butyl-4-hydroxyphenyl) propionamide], 2,4-dimethyl -6-(1-methylpentadecyl) phenol, diethyl [[3,5-bis(1,1-dimethylethyl) -4-hydroxyphenyl]methyl]phosphoate, 3,3',3'',5,5',5''-hexa-tert-butyl-α,α',α''-(mesitylen-2,4,6-triyl)tri-p-cresol, 4,6-bis(octylthiomethyl)-o-cresol, ethylenebis (oxyethylene)bis[3-(5-tert-butyl-4-hydroxy-m-tolyl) propionate], hexamethylenebis[3-(3,5-di-tert-butyl-4-hydroxyphenyl)propionate], 1,3,5-tris(3,5-di-tert-butyl-4-hydroxybenzyl) -1,3,5-triazine-2,4,6(1H,3H,5H)-trione, 2,6-di-tert -butyl-4-(4,6-bis(octylthio)-1,3,5-triazin-2-ylamino)phenol, and 2-[1-(2-hydroxy-3,5-di-tert-pentylphenyl)ethyl]-4,6-di-tert-pentylphenyl acrylate.

Pentaerythritol tetrakis[3-(3,5-di-tert-butyl-4-hydroxyphenyl)propionate] and octadecyl 3-(3,5-di-tert-butyl-4-hydroxyphenyl)propionate are preferred among the preceding. These phenolic oxidation inhibitors can be specifically exemplified by "Irganox 1010" and "Irganox 1076" from BASF and "ADK STAB AO-50" and "ADK STAB AO-60" from the ADEKA Corporation.

A single phenolic stabilizer may be incorporated or any combination of two or more in any proportions may be incorporated.

The content of the phenolic stabilizer, per 100 parts by mass of the polycarbonate resin (A), is 0.01 to 0.5 parts by mass and is preferably at least 0.02 parts by mass and more preferably at least 0.03 parts by mass and is preferably not more than 0.4 parts by mass, more preferably not more than 0.3 parts by mass, and still more preferably not more than 0.2 parts by mass. The effect as a phenolic stabilizer may be unsatisfactory when the phenolic stabilizer content is less than the lower limit for the indicated range. When the phenolic stabilizer content exceeds the upper limit for the indicated range, the effect hits a ceiling and this may thus be uneconomical.

A phosphorus stabilizer may be used in combination with a phenolic stabilizer. In such an instance, the total content of the phosphorus stabilizer and phenolic stabilizer, per 100 parts by mass of the polycarbonate resin (A), is 0.01 to 0.5 parts by mass and is preferably at least 0.02 parts by mass and more preferably at least 0.03 parts by mass and is preferably not more than 0.4 parts by mass, more preferably not more than 0.3 parts by mass, and still more preferably not more than 0.2 parts by mass.

[Sulfur Stabilizer]

The sulfur stabilizer can be exemplified by dilauryl 3,3'-thiodipropionate, ditridecyl 3,3'-thiodipropionate, dimyristyl 3,3'-thiodipropionate, distearyl 3,3'-thiodipropionate, lauryl stearyl 3,3'-thiodipropionate, pentaerythritol tetrakis (3-laurylthiopropionate), bis[2-methyl -4-(3-laurylthiopropionyloxy)-5-tert-butylphenyl] sulfide, octadecyl disulfide, mercaptobenzimidazole, 2-mercapto -6-methylbenzimidazole, and 1,1'-thiobis(2-naphthol).

Pentaerythritol tetrakis(3-laurylthiopropionate) is preferred among the preceding. This sulfur stabilizer can be specifically exemplified by "ADK STAB AO-412S" from the ADEKA Corporation.

The content of the sulfur stabilizer, per 100 parts by mass of the polycarbonate resin (A), is 0.01 to 0.5 parts by mass and is preferably at least 0.02 parts by mass and more preferably at least 0.03 parts by mass and is preferably not more than 0.4 parts by mass, more preferably not more than 0.3 parts by mass, and still more preferably not more than 0.2 parts by mass. The effect as a sulfur stabilizer may be unsatisfactory when the sulfur stabilizer content is less than the lower limit for the indicated range. When the sulfur stabilizer content exceeds the upper limit for the indicated range, the effect hits a ceiling and this may thus be uneconomical.

[Additives]

The polycarbonate resin composition according to the first invention may contain additives other than those described above, for example, additives such as mold-release agents, fluorescent brighteners, pigments, dyes, flame retardants, impact resistance enhancers, antistatic agents, plasticizers, compatibilizers, and so forth, and may contain a polymer other than a polycarbonate resin. A single one of these additives or two or more of these additives may be incorporated, while a single additional resin or two or more additional resins may be incorporated. The polycarbonate resin composition according to the second invention may also contain additives other than those described above, and their type, content, and so forth are the same as for the first invention.

Second Invention

The second invention is described in the following.

The second invention relates to the polycarbonate resin composition and molded article described in the following.

[1] A polycarbonate resin composition comprising, per 100 parts by mass of a polycarbonate resin (A), 0.08 to 1 parts by mass of an ultraviolet absorber (B2) having a maximum absorption wavelength of at least 360 nm and less than 375 nm in the absorption curve determined according to JIS K 7105 using the following formula, and 0.01 to 0.5 parts by mass of a stabilizer (C).

[absorbance of the polycarbonate resin that contains 0.005% by mass of the ultraviolet absorber]–
[absorbance of only the polycarbonate resin]

[2] The polycarbonate resin composition according to [1], wherein the ultraviolet absorber (B2) is a sesamol group-containing benzotriazole ultraviolet absorber.

[3] The polycarbonate resin composition according to [1] or [2], wherein the ultraviolet absorber (B2) is an ultraviolet absorber represented by the following general formula (2).

[C6]

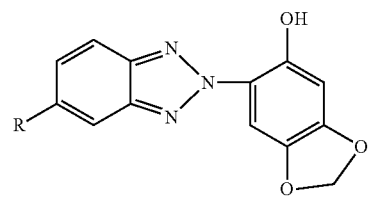

(2)

(In the formula, R represents a hydrogen atom, alkyl group having 1 to 8 carbon atoms, alkoxy group having 1 to 8 carbon atoms, hydroxyl group, carboxyl group, alkyloxycarbonyl group having 1 to 8 carbon atoms in the alkyl group, hydroxyalkyl group having 1 to 8 carbon atoms, or alkylcarbonyloxyalkyl group having 1 to 8 carbon atoms in each of the alkyl groups.)

[4] The polycarbonate resin composition according to any of [1] to [3], that additionally contains, per 100 parts by mass of the polycarbonate resin (A), 0.01 to 0.2 parts by mass of (B3) an ultraviolet absorber having a maximum absorption wavelength of less than 360 nm in the absorption curve determined according to JIS K 7105 using the following formula.

[5] The polycarbonate resin composition according to [4], wherein the ultraviolet absorber (B3) is at least one selection from benzotriazole ultraviolet absorbers lacking sesamol group, triazine ultraviolet absorbers, malonate ester ultraviolet absorbers, and benzoxazine ultraviolet absorbers.

[6] The polycarbonate resin composition according to any of [1] to [5], wherein the transmittance measured according to JIS K 7105 at a wavelength of 420 nm on a 2 mm-thick molded article is not greater than 25%.

[7] A molded article of the polycarbonate resin composition according to any one of [1] to [6].

The individual components themselves used in the polycarbonate resin composition according to the second invention are substantially the same components as those described for the first invention of the present invention, and, unless specifically indicated otherwise, the description for the first invention as provided above directly applies to the individual components per se used in the second invention.

[Polycarbonate Resin (A)]

The polycarbonate resin (A) is as has been described above, and the same description is also applied to the polycarbonate resin (A) according to the second invention.

[Ultraviolet Absorber (B2)]

The polycarbonate resin composition according to the second invention contains an ultraviolet absorber (B2) having a maximum absorption wavelength of at least 360 nm and less than 375 nm in the absorption curve determined according to JIS K 7105 using the following formula (1).

[absorbance of the polycarbonate resin that contains
0.005% by mass of the ultraviolet absorber]–
[absorbance of only the polycarbonate resin]     (1)

The ultraviolet absorber (B2) is as has been described above, and the same description is also applied to the ultraviolet absorber (B2) according to the second invention.

The content of the ultraviolet absorber (B2) is 0.08 to 1 parts by mass per 100 parts by mass of the polycarbonate resin (A). When this content is less than 0.08 parts by mass, the transmittance of the resulting resin composition in the 400 to 420 nm wavelength region is then too high. When this content exceeds 1 parts by mass, the transmittance in the 400 to 420 nm wavelength region is low, but gas generation during molding becomes substantial and the volatile fraction adheres to the molded article and the appearance of the product is then substantially impaired. The content of the ultraviolet absorber (B2) per 100 parts by mass of the polycarbonate resin (A) is preferably 0.08 to 0.9 parts by mass, more preferably 0.08 to 0.8 parts by mass, still more preferably 0.08 to 0.7 parts by mass, and particularly preferably 0.08 to 0.6 parts by mass.

[Ultraviolet Absorber (B3)]

The polycarbonate resin composition according to the second invention preferably additionally contains (B3) an ultraviolet absorber having a maximum absorption wavelength of less than 360 nm in the absorption curve determined according to JIS K 7105 from formula (1).

The incorporation of the ultraviolet absorber (B3) makes it possible to ameliorate the trend wherein the transmittance around 320 nm is prone to increase when the content of the ultraviolet absorber (B2) is relatively small.

With regard to this ultraviolet absorber (B3), the description of the ultraviolet absorber (B3) for the first invention is also likewise applied to the ultraviolet absorber (B3) for the second invention.

The preferred content of the ultraviolet absorber (B3) is from 0.01 to 0.2 parts by mass per 100 parts by mass of the polycarbonate resin (A). Transmission around the 320 nm wavelength by the resulting resin composition readily occurs at less than 0.01 parts by mass, while at above 0.2 parts by mass the occurrence of gas generation during molding is facilitated and the product appearance is readily impaired. The content of the ultraviolet absorber (B3) per 100 parts by mass of the polycarbonate resin (A) is more preferably at least 0.02 parts by mass and still more preferably at least 0.03 parts by mass and is more preferably not more than 0.15 parts by mass.

[Stabilizer (C)]

The polycarbonate resin composition according to the second invention contains a stabilizer (C). This stabilizer (C) can be exemplified by phosphorus stabilizers, phenolic stabilizers, sulfur stabilizers, and so forth.

The stabilizer (C) used in the second invention is the same as in the first invention with regard to type, content, and so forth, and the previous description likewise applies to the stabilizer (C) according to the second invention.

[Additives]

The polycarbonate resin composition according to the second invention may contain additives other than those described above, for example, additives such as mold-release agents, antioxidants, fluorescent brighteners, pigments, dyes, flame retardants, impact resistance enhancers, antistatic agents, plasticizers, compatibilizers, and so forth, and may contain a polymer other than a polycarbonate resin. A single one of these additives or two or more of these additives may be incorporated, while a single additional resin or two or more additional resins may be incorporated.

[Method for Producing Polycarbonate Resin Composition]

There are no limitations on the method for producing the polycarbonate resin composition according to the present invention, and the known methods for producing polycarbonate resin compositions may be broadly adopted. The method can be exemplified by preliminarily mixing, by use any of various mixers such as, for example, a tumbler or a Henschel mixer, the polycarbonate resin (A), ultraviolet absorber (B1) or (B2), phosphorus stabilizer (C), and other components blended on an optional basis, followed by melt kneading using a mixer such as a Banbury mixer, roll, Brabender, single-screw kneading extruder, twin-screw kneading extruder, kneader, and so forth. The melt kneading temperature is not particularly limited, but is generally in the range from 240° C. to 320° C.

A variety of molded articles can be produced from the polycarbonate resin composition according to the present invention by pelletizing the polycarbonate resin composition described in the preceding and molding the pellets using any of various molding methods. In addition, the method need not proceed through a pellet stage, and the molded article may also be made by directly molding the resin that has been melt kneaded in an extruder.

The transmittance measured at a wavelength of 420 nm according to JIS K 7105 on a 2 mm-thick molded article obtained by molding the polycarbonate resin composition according to the present invention is preferably not more than 25%, more preferably not more than 10%, even more preferably not more than 5%, and particularly preferably not more than 1%. When the transmittance at a wavelength of 420 nm exceeds 25%, the performance as a material intended to block the 400 to 420 nm wavelength region, e.g., as a sunglass lens and so forth, is then unsatisfactory.

Molded articles obtained from the polycarbonate resin composition according to the present invention exhibit an excellent ability to block ultraviolet light as well as light at wavelengths of 400 to 420 nm, which is on the visible light side therefrom; are free of the problem of gas generation during molding; and have the various excellent mechanical and thermal properties exhibited by polycarbonate resins. They can therefore be broadly and advantageously used in applications where ultraviolet radiation-induced deterioration is a concern, for example, for sheet, film, general goods, components for consumer electronics and electrical appliances, automotive parts, building materials, hollow containers, and so forth. More specifically, eyeglass lenses, sunglass lenses, goggles (for skiing), protective eyeglasses, protective masks, and so forth; roof panels for arcades, indoor pools, carports, sun roofs, and so forth; as well as signal lamps, sound insulating walls, side windows and rear windows for automobiles, solar cell housings, street lamp covers, and so forth, are preferred examples.

EXAMPLES

The present invention is more specifically described in the following using examples. However, the present invention should not be construed as being limited to or by the following examples.

Examples and Comparative Examples for First Invention

The starting materials and evaluation methods used in the following examples and comparative examples for the first invention are as follows.

TABLE 1

| component | | designation |
|---|---|---|
| polycarbonate resin (A) | bisphenol A aromatic polycarbonate resin<br>Mitsubishi Engineering-Plastics Corporation<br>product name: "Iupilon (registered trademark) S-3000"<br>viscosity-average molecular weight Mv: 22,000 | A-1 |
| ultraviolet absorber (B1) | 6-(5-chloro-2H-benzotriazol-2-yl)benzo[1,3]dioxol-5-ol<br>Shipro Kasei Kaisha, Ltd.<br>maximum absorption wavelength: 378 nm | B1-1 |
| ultraviolet absorber (B2) | 6-(2H-benzotriazol-2-yl)benzo[1,3]dioxol-5-ol<br>Shipro Kasei Kaisha, Ltd.<br>maximum absorption wavelength: 368 nm | B2-1 |
| ultraviolet absorber (B3) | 2-[5-chloro(2H)-benzotriazol-2-yl]-4-methyl-6-(t-butyl)phenol<br>BASF, product name: "Tinuvin 326"<br>maximum absorption wavelength: 355 nm | B3-1 |
| | 2-(2-hydroxy-5-t-octylphenyl)-2H-benzotriazole<br>Shipro Kasei Kaisha, Ltd., product name: "SEESORB 709"<br>maximum absorption wavelength: 344 nm | B3-2 |
| | 2,2'-methylenebis[6-(2H-benzotriazol-2-yl)-4-(1,1,3,3-tetramethylbutyl)phenol]<br>ADEKA Corporation, product name: "ADK STAB LA-31"<br>maximum absorption wavelength: 349 nm | B3-3 |
| | 2-(4,6-diphenyl-1,3,5-triazin-2-yl)-5-[(hexyl)oxy]phenol<br>BASF, product name: "Tinuvin 1577FF"<br>maximum absorption wavelength: 274 nm | B3-4 |
| | 2,2'-(1,4-phenylene)bis(4H-3,1-benzoxazin-4-one)<br>Cytec, product name: "Cyasorb UV3638"<br>maximum absorption wavelength: 348 nm | B3-5 |
| | tetraethyl 2,2'-(1,4-phenylenedimethylidene)bismalonate<br>Clariant Japan KK, product name: "Hostavin B-CAP"<br>maximum absorption wavelength: 320 nm | B3-6 |
| phosphorus stabilizer (C) | bis(2,6-di-t-butyl-4-methylphenyl) pentaerythritol diphosphite<br>ADEKA Corporation, product name: "ADK STAB PEP-36" | C-1 |
| | bis(2,4-dicumylphenyl) pentaerythritol diphosphite<br>Dover Chemical Corporation,<br>product name: "DOVERPHOS S-9228PC" | C-2 |
| phenolic stabilizer (D) | octadecyl 3-(3,5-di-t-butyl-4-hydroxyphenyl) propionate<br>ADEKA Corporation, product name: "ADK STAB AO-50" | D-1 |

With regard to the maximum absorption wavelength for the ultraviolet absorber given in Table 1, the absorbance $A_\lambda$ was determined for the composition provided by the incorporation of 0.005% of the particular ultraviolet absorber into the polycarbonate resin given in Table 1, and the absorbance $A_{\lambda,0}$ was determined for the polycarbonate resin given in Table 1 without the incorporation of the ultraviolet absorber. The maximum absorption wavelength is obtained from the absorption curve for the $(A_\lambda - A_{\lambda,0})$ absorbance provided by subtracting the absorbance $A_{\lambda,0}$ from the absorbance $A_\lambda$. The measurement of the absorbance $A_\lambda$ and the absorbance $A_{\lambda,0}$ was carried out using the method described below in [Measurement of Transmittance and Absorbance].

Examples 1 to 22 and Comparative Examples 1 to 9

[Production of Resin Composition Pellets]

The components given in Table 1 were blended in the proportions (parts by mass) indicated in Tables 2 to 4 and were mixed for 20 minutes with a tumbler. This was followed by melt kneading at a cylinder temperature of 280° C. with a vented single-screw extruder having a screw diameter of 40 mm ("VS-40" from Tanabe Plastics Machinery Co., Ltd.) and production of pellets of the polycarbonate resin composition by strand cutting.

[Measurement of Transmittance and Absorbance]

The obtained pellets were dried for 5 hours at 120° C. using a hot-air circulation dryer followed by the molding of stepped flat plate-shaped test specimens of width 50 mm×length 90 mm×three thickness stages of 1 mm, 2 mm, and 3 mm. The molding was performed with an injection molder ("SE50DUZ" from Sumitomo Heavy Industries, Ltd.) using conditions of a resin temperature of 280° C., a mold temperature of 80° C., and a mold cycle of 30 seconds.

The transmittance and absorbance were measured according to JIS K 7105 on the 2 mm-thick region of the stepped flat plate-shaped test specimen using a spectrophotometer ("UV-3100PC" from the Shimadzu Corporation).

The transmittance (unit: %) at 420 nm, 380 nm, and 320 nm is given in Tables 2 to 4.

[Evaluation of Gas Generation During Molding]

The obtained pellets were dried for 5 hours at 120° C. and were subsequently injection molded for 100 shots using an injection molder ("SE18DUZ" from Sumitomo Heavy Industries, Ltd.) and the drop-shaped mold shown in FIG. 1 and using conditions of a cylinder temperature of 320° C., a mold cycle of 10 seconds, and a mold temperature of 80° C. After completion, the gas generation during molding was evaluated by visually evaluating and scoring, by use of the following criteria based on a comparison with Comparative Example 2, the state of contamination by white deposits generated on the metal mirror surface on the mold cavity side.

A: Mold deposition is much less than the condition after molding for 100 shots in Comparative Example 2 and the resistance to mold contamination is thus very good.

B: Mold deposition is less than the condition after molding for 100 shots in Comparative Example 2 and resistance to mold contamination is seen to some degree.

C: Mold deposition is on the same level as the condition after molding for 100 shots in Comparative Example 2 and mold contamination is thus observed.

D: Mold deposition is larger than the condition after molding for 100 shots in Comparative Example 2 and mold contamination is thus observed to a substantial degree.

Comparative Example 2 has the same level of mold deposition as Comparative Example 13 according to the second invention, infra.

With reference to the drop-shaped mold in FIG. 1, the resin composition is introduced through the gate G, and the mold is designed to facilitate the collection of generated gas in the tip region P. The gate G has a width of 1 mm and a thickness of 1 mm; in FIG. 1, the width h1 is 14.5 mm, the length h2 is 7 mm, the length h3 is 27 mm, and the thickness of the mold region is 3 mm.

The results of the preceding evaluations are given in Tables 2 to 4.

TABLE 2

| component | example 1 | 2 | 3 | 4 | 5 | 6 | 7 | 8 | 9 | 10 | 11 |
|---|---|---|---|---|---|---|---|---|---|---|---|
| A-1 | 100 | 100 | 100 | 100 | 100 | 100 | 100 | 100 | 100 | 100 | 100 |
| B1-1 | 0.07 | 0.07 | 0.07 | 0.07 | 0.08 | 0.07 | 0.07 | 0.05 | 0.05 | 0.04 | 0.03 |
| B2-1 | | | | | | 0.03 | 0.03 | | | | |
| B3-1 | | | | 0.05 | | | | | | | |
| B3-2 | | 0.05 | 0.05 | | 0.05 | | 0.05 | | 0.1 | 0.1 | 0.1 |
| B3-3 | | | | | | | | | | | |
| B3-4 | | | | | | | | | | | |
| B3-5 | | | | | | | | | | | |
| B3-6 | | | | | | | | | | | |
| C-1 | 0.1 | 0.1 | 0.1 | 0.1 | 0.1 | 0.1 | 0.1 | 0.1 | 0.1 | 0.1 | 0.1 |
| C-2 | | | | | | | | | | | |
| D-1 | | | | 0.05 | 0.05 | 0.05 | | | | | |
| transmittance (%) at 420 nm | 0.6 | 0.6 | 0.6 | 0.5 | 0.3 | 0.3 | 0.3 | 2.5 | 2.5 | 10 | 20 |
| transmittance (%) at 380 nm | 0 | 0 | 0 | 0 | 0 | 0 | 0 | 0 | 0 | 0 | 0 |
| transmittance (%) at 320 nm | 0.4 | 0 | 0 | 0 | 0 | 0 | 0 | 1.4 | 0 | 0 | 0 |
| gas generation during molding | A | A | A | A | A | A | A | A | A | A | A |

TABLE 3

| component | example 12 | 13 | 14 | 15 | 16 | 17 | 18 | 19 | 20 | 21 | 22 |
|---|---|---|---|---|---|---|---|---|---|---|---|
| A-1 | 100 | 100 | 100 | 100 | 100 | 100 | 100 | 100 | 100 | 100 | 100 |
| B1-1 | 0.1 | 0.5 | 0.07 | 0.07 | 0.07 | 0.07 | 0.07 | 0.07 | 0.07 | 0.07 | 0.07 |
| B2-1 | | | | | | | | | | | |
| B3-1 | | | | | | | | | | | |
| B3-2 | | | | 0.05 | 0.05 | | 0.05 | | | | |
| B3-3 | | | | | | | | 0.05 | | | |
| B3-4 | | | | | | | | | 0.05 | | |
| B3-5 | | | | | | | | | | 0.05 | |
| B3-6 | | | | | | | | | | | 0.05 |
| C-1 | 0.1 | 0.1 | | | | | | 0.1 | 0.1 | 0.1 | 0.1 |
| C-2 | | | 0.1 | 0.1 | 0.1 | | | | | | |
| D-1 | | | | | 0.05 | 0.05 | 0.05 | | | | |
| transmittance (%) at 420 nm | 0.1 | 0 | 0.6 | 0.6 | 0.6 | 0.6 | 0.6 | 0.6 | 0.6 | 0.6 | 0.6 |
| transmittance (%) at 380 nm | 0 | 0 | 0 | 0 | 0 | 0 | 0 | 0 | 0 | 0 | 0 |
| transmittance (%) at 320 nm | 0 | 0 | 0.4 | 0 | 0 | 0.4 | 0 | 0 | 0 | 0 | 0 |
| gas generation during molding | A | B | A | A | A | A | A | A | A | A | A |

TABLE 4

| component | comparative example 1 | 2 | 3 | 4 | 5 | 6 | 7 | 8 | 9 |
|---|---|---|---|---|---|---|---|---|---|
| A-1 | 100 | 100 | 100 | 100 | 100 | 100 | 100 | 100 | 100 |
| B1-1 | 0.01 | 2 | | | | | | | |
| B2-1 | | | 0.03 | | | | | | |
| B3-1 | | | | 0.05 | 0.5 | 2 | 4.5 | | |
| B3-2 | | | | | | | | 0.3 | 2 |
| B3-3 | | | | | | | | | |
| B3-4 | | | | | | | | | |
| B3-5 | | | | | | | | | |
| B3-6 | | | | | | | | | |
| C-1 | 0.1 | 0.1 | 0.1 | 0.1 | 0.1 | 0.1 | 0.1 | 0.1 | 0.1 |
| C-2 | | | | | | | | | |
| D-1 | | | | | | | | | |
| transmittance (%) at 420 nm | 70 | 0 | 72 | 82 | 53 | 13 | 1 | 90 | 80 |
| transmittance (%) at 380 nm | 50 | 0 | 3 | 0 | 0 | 0 | 0 | 0 | 0 |
| transmittance (%) at 320 nm | 20 | 0 | 10 | 0 | 0 | 0 | 0 | 0 | 0 |
| gas generation during molding | A | C | A | A | B | C | D | B | B |

Examples and Comparative Examples for Second Invention

The starting materials and evaluation methods used in the following examples and comparative examples for the second invention are as follows.

TABLE 5

| component | | designation |
|---|---|---|
| polycarbonate resin (A) | bisphenol A aromatic polycarbonate resin<br>Mitsubishi Engineering-Plastics Corporation<br>product name: "Iupilon (registered trademark) S-3000"<br>viscosity-average molecular weight Mv: 22,000 | A-1 |
| ultraviolet absorber (B2) | 6-(2H-benzotriazol-2-yl)benzo[1,3]dioxol-5-ol<br>Shipro Kasei Kaisha, Ltd.<br>maximum absorption wavelength: 368 nm | B2-1 |
| | 6-(5-n-heptylcarbonyloxyethyl-2H-benzotriazol-2-yl)benzo[1,3]dioxol-5-ol<br>Shipro Kasei Kaisha, Ltd.<br>maximum absorption wavelength: 372 nm | B2-2 |
| | 6-(5-isoheptylcarbonyloxyethyl-2H-benzotriazol-2-yl)benzo[1,3]dioxol-5-ol<br>Shipro Kasei Kaisha, Ltd.<br>maximum absorption wavelength: 372 nm | B2-3 |
| ultraviolet absorber (B3) | 2-[5-chloro(2H)-benzotriazol-2-yl]-4-methyl-6-(t-butyl)phenol<br>BASF, product name: "Tinuvin 326"<br>maximum absorption wavelength: 355 nm | B3-1 |
| | 2-(2-hydroxy-5-t-octylphenyl)-2H-benzotriazole<br>Shipro Kasei Kaisha, Ltd., product name: "SEESORB 709"<br>maximum absorption wavelength: 344 nm | B3-2 |
| | 2,2'-methylenebis[6-(2H-benzotriazol-2-yl)-4-(1,1,3,3-tetramethylbutyl)phenol]<br>ADEKA Corporation, product name: "ADK STAB LA-31"<br>maximum absorption wavelength: 349 nm | B3-3 |
| | 2-(4,6-diphenyl-1,3,5-triazin-2-yl)-5-[(hexyl)oxy]phenol<br>BASF, product name: "Tinuvin 1577FF"<br>maximum absorption wavelength: 274 nm | B3-4 |
| | 2,2'-(1,4-phenylene)bis(4H-3,1-benzoxazin-4-one)<br>Cytec, product name: "Cyasorb UV3638"<br>maximum absorption wavelength: 348 nm | B3-5 |
| | tetraethyl 2,2'-(1,4-phenylenedimethylidene)bismalonate<br>Clariant Japan KK, product name: "Hostavin B-CAP"<br>maximum absorption wavelength: 320 nm | B3-6 |
| phosphorus stabilizer (C) | bis(2,6-di-t-butyl-4-methylphenyl) pentaerythritol diphosphite<br>ADEKA Corporation, product name: "ADK STAB PEP-36" | C-1 |
| | bis(2,4-dicumylphenyl) pentaerythritol diphosphite<br>Dover Chemical Corporation, product name: "DOVERPHOS S-9228PC" | C-2 |
| phenolic stabilizer (D) | octadecyl 3-(3,5-di-t-butyl-4-hydroxyphenyl) propionate<br>ADEKA Corporation, product name: "ADK STAB AO-50" | D-1 |

With regard to the maximum absorption wavelength for the ultraviolet absorber given in Table 5, the absorbance $A_\lambda$ was determined for the composition provided by the incorporation of 0.005% of the particular ultraviolet absorber into the polycarbonate resin given in Table 5, and the absorbance $A_{\lambda,0}$ was determined for the polycarbonate resin given in Table 5 without the incorporation of the ultraviolet absorber. The maximum absorption wavelength is obtained from the absorption curve for the $(A_\lambda - A_{\lambda,0})$ absorbance provided by subtracting the absorbance $A_{\lambda,0}$ from the absorbance $A_\lambda$. The measurement of the absorbance $A_\lambda$ and the absorbance $A_{\lambda,0}$ was carried out using the method described below in [Measurement of Transmittance and Absorbance].

Examples 23 to 45 and Comparative Examples 10 to 21

[Production of Resin Composition Pellets]

The components given in Table 5 were blended in the proportions (parts by mass) indicated in Table 6 and were mixed for 20 minutes with a tumbler. This was followed by melt kneading at a cylinder temperature of 280° C. with a vented single-screw extruder having a screw diameter of 40 mm ("VS-40" from Tanabe Plastics Machinery Co., Ltd.) and production of pellets of the polycarbonate resin composition by strand cutting.

[Measurement of Transmittance and Absorbance]

The obtained pellets were dried for 5 hours at 120° C. using a hot-air circulation dryer followed by the molding of stepped flat plate-shaped test specimens of width 50 mm×length 90 mm×three thickness stages of 1 mm, 2 mm, and 3 mm. The molding was performed with an injection molder ("SE50DUZ" from Sumitomo Heavy Industries, Ltd.) using conditions of a resin temperature of 280° C., a mold temperature of 80° C., and a mold cycle of 30 seconds.

The transmittance and absorbance were measured according to JIS K 7105 on the 2 mm-thick region of the stepped flat plate-shaped test specimen using a spectrophotometer ("UV-3100PC" from the Shimadzu Corporation).

The transmittance (unit: %) at 420 nm, 380 nm, and 320 nm is given in Table 6.

[Evaluation of Gas Generation During Molding]

The obtained pellets were dried for 5 hours at 120° C. and were subsequently injection molded for 100 shots using an injection molder ("SE18DUZ" from Sumitomo Heavy Industries, Ltd.) and the drop-shaped mold shown in FIG. 1 and using conditions of a cylinder temperature of 320° C., a mold cycle of 10 seconds, and a mold temperature of 80° C. After completion, the gas generation during molding was evaluated by visually evaluating and scoring, by use of the following criteria based on a comparison with Comparative Example 13, the state of contamination by white deposits generated on the metal mirror surface on the mold cavity side.

A: Mold deposition is much less than the condition after molding for 100 shots in Comparative Example 13 and the resistance to mold contamination is thus very good.

B: Mold deposition is less than the condition after molding for 100 shots in Comparative Example 13 and resistance to mold contamination is seen to some degree.

C: Mold deposition is on the same level as the condition after molding for 100 shots in Comparative Example 13 and mold contamination is thus observed.

D: Mold deposition is larger than the condition after molding for 100 shots in Comparative Example 13 and mold contamination is thus observed to a substantial degree.

Comparative Example 13 has the same level of mold deposition as Comparative Example 2 according to the first invention, supra.

With reference to the drop-shaped mold in FIG. 1, the resin composition is introduced through the gate G, and the mold is designed to facilitate the collection of generated gas in the tip region P. The gate G has a width of 1 mm and a thickness of 1 mm; in FIG. 1, the width h1 is 14.5 mm, the length h2 is 7 mm, the length h3 is 27 mm, and the thickness of the mold region is 3 mm.

The results of the preceding evaluations are given in Table 6.

TABLE 6

| component | example | | | | | | | | | |
|---|---|---|---|---|---|---|---|---|---|---|
| | 23 | 24 | 25 | 26 | 27 | 28 | 29 | 30 | 31 | 32 |
| A-1 | 100 | 100 | 100 | 100 | 100 | 100 | 100 | 100 | 100 | 100 |
| B2-1 | 0.09 | 0.15 | 0.25 | 0.5 | | | 0.07 | 0.07 | 0.1 | 0.1 |
| B2-2 | | | | | 0.4 | | 0.02 | | 0.05 | |
| B2-3 | | | | | | 0.4 | | 0.02 | | 0.05 |
| B3-1 | | | | | | | | | | |
| B3-2 | | | | | | | | | | |
| B3-3 | | | | | | | | | | |
| B3-4 | | | | | | | | | | |
| B3-5 | | | | | | | | | | |
| B3-6 | | | | | | | | | | |
| C-1 | 0.1 | 0.1 | 0.1 | 0.1 | 0.1 | 0.1 | 0.1 | 0.1 | 0.1 | 0.1 |
| C-2 | | | | | | | | | | |
| D-1 | | | | | | | | | | |
| transmittance (%) at 420 nm | 20 | 10 | 0.9 | 0 | 0.1 | 0.2 | 20 | 20 | 10 | 10 |
| transmittance (%) at 380 nm | 0 | 0 | 0 | 0 | 0 | 0 | 0 | 0 | 0 | 0 |
| transmittance (%) at 320 nm | 0 | 0 | 0 | 0 | 0 | 0 | 0 | 0 | 0 | 0 |
| gas generation during molding | A | B | B | B | B | B | A | A | B | B |

TABLE 7

| component | \multicolumn{13}{c}{example} |
| --- | --- | --- | --- | --- | --- | --- | --- | --- | --- | --- | --- | --- | --- |
|  | 33 | 34 | 35 | 36 | 37 | 38 | 39 | 40 | 41 | 42 | 43 | 44 | 45 |
| A-1 | 100 | 100 | 100 | 100 | 100 | 100 | 100 | 100 | 100 | 100 | 100 | 100 | 100 |
| B2-1 | 0.09 | 0.09 | 0.09 | 0.09 | 0.07 | 0.07 | 0.09 | 0.15 | 0.09 | 0.09 | 0.09 | 0.09 | 0.09 |
| B2-2 |  |  |  |  | 0.02 |  |  |  |  |  |  |  |  |
| B2-3 |  |  |  |  |  | 0.02 |  |  |  |  |  |  |  |
| B3-1 |  |  | 0.15 |  |  |  |  |  |  |  |  |  |  |
| B3-2 |  |  |  | 0.15 | 0.15 | 0.15 |  |  | 0.15 |  |  |  |  |
| B3-3 |  |  |  |  |  |  |  |  |  | 0.15 |  |  |  |
| B3-4 |  |  |  |  |  |  |  |  |  |  | 0.15 |  |  |
| B3-5 |  |  |  |  |  |  |  |  |  |  |  | 0.15 |  |
| B3-6 |  |  |  |  |  |  |  |  |  |  |  |  | 0.15 |
| C-1 |  | 0.1 | 0.1 | 0.1 | 0.1 | 0.1 |  |  | 0.1 | 0.1 | 0.1 | 0.1 | 0.1 |
| C-2 | 0.1 |  |  |  |  |  |  |  |  |  |  |  |  |
| D-1 |  | 0.05 |  |  |  |  | 0.05 | 0.05 | 0.05 |  |  |  |  |
| transmittance (%) at 420 nm | 20 | 20 | 20 | 20 | 20 | 20 | 20 | 10 | 20 | 20 | 20 | 20 | 20 |
| transmittance (%) at 380 nm | 0 | 0 | 0 | 0 | 0 | 0 | 0 | 0 | 0 | 0 | 0 | 0 | 0 |
| transmittance (%) at 320 nm | 0 | 0 | 0 | 0 | 0 | 0 | 0 | 0 | 0 | 0 | 0 | 0 | 0 |
| gas generation during molding | A | A | B | B | B | B | A | B | B | B | B | B | B |

TABLE 8

| component | \multicolumn{12}{c}{comparative example} |
| --- | --- | --- | --- | --- | --- | --- | --- | --- | --- | --- | --- | --- |
|  | 10 | 11 | 12 | 13 | 14 | 15 | 16 | 17 | 18 | 19 | 20 | 21 |
| A-1 | 100 | 100 | 100 | 100 | 100 | 100 | 100 | 100 | 100 | 100 | 100 | 100 |
| B2-1 | 0.06 |  |  | 2 |  |  |  |  |  |  |  |  |
| B2-2 |  | 0.07 |  |  | 2 |  |  |  |  |  |  |  |
| B2-3 |  |  | 0.07 |  |  | 2 |  |  |  |  |  |  |
| B3-1 |  |  |  |  |  |  | 0.05 | 0.5 | 2 | 4.5 |  |  |
| B3-2 |  |  |  |  |  |  |  |  |  |  | 0.05 | 0.3 |
| B3-3 |  |  |  |  |  |  |  |  |  |  |  |  |
| B3-4 |  |  |  |  |  |  |  |  |  |  |  |  |
| B3-5 |  |  |  |  |  |  |  |  |  |  |  |  |
| B3-6 |  |  |  |  |  |  |  |  |  |  |  |  |
| C-1 | 0.1 | 0.1 | 0.1 | 0.1 | 0.1 | 0.1 | 0.1 | 0.1 | 0.1 | 0.1 | 0.1 | 0.1 |
| C-2 |  |  |  |  |  |  |  |  |  |  |  |  |
| D-1 |  |  |  |  |  |  |  |  |  |  |  |  |
| transmittance (%) at 420 nm | 30 | 30 | 30 | 0 | 0 | 0 | 82 | 53 | 13 | 1 | 90 | 90 |
| transmittance (%) at 380 nm | 0 | 0 | 0 | 0 | 0 | 0 | 0 | 0 | 0 | 0 | 13 | 0 |
| transmittance (%) at 320 nm | 1 | 1 | 1 | 0 | 0 | 0 | 0 | 0 | 0 | 0 | 0 | 0 |
| gas generation during molding | A | A | A | C | C | C | A | B | C | D | A | B |

INDUSTRIAL APPLICABILITY

Molded articles obtained from the polycarbonate resin composition according to the present invention exhibit an excellent ability to block ultraviolet light as well as light on the visible light side therefrom at wavelengths of 400 to 420 nm; are free of the problem of gas generation during molding; and have the various excellent mechanical and thermal properties exhibited by polycarbonate resins. They can therefore be advantageously used in applications where ultraviolet radiation-induced deterioration is a concern and thus have a high level of industrial applicability.

The invention claimed is:

1. A polycarbonate resin composition, comprising:
a polycarbonate resin (A) and, per 100 parts by mass of the polycarbonate resin (A);
from 0.02 to 0.1 parts by mass of a first sesamol group-comprising benzotriazole ultraviolet absorber (B1) of formula (1)

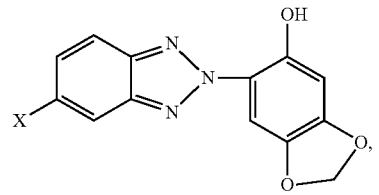
(1)

X being a halogen atom, and the first ultraviolet absorber (B1) having a maximum absorption wavelength of at least 375 nm in an absorption curve determined according to JIS K 7105 using formula (x), below; and

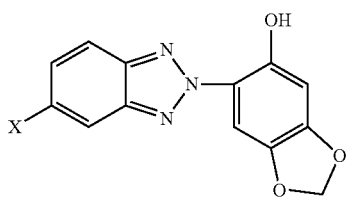

from 0.01 to 0.5 parts by mass of a stabilizer (C),
wherein the formula (x) is

[an absorbance of the polycarbonate resin (A) comprising 0.005% by mass of the first ultraviolet absorber (B1)]– [an absorbance of the polycarbonate resin (A)].

2. The composition of claim 1, further comprising:
from 0.08 to 1 parts by mass of a second sesamol group comprising benzotriazole ultraviolet absorber (B2), per 100 parts by mass of the polycarbonate resin (A), having a maximum absorption wavelength of at least 360 nm and less than 375 nm in the absorption curve determined according to JIS K 7105 using formula

[an absorbance of the polycarbonate resin (A) comprising 0.005% by mass of the second ultraviolet absorber (B2)]– [an absorbance of the polycarbonate resin (A)].

3. The composition of claim 2, wherein the ultraviolet absorber (B2) has formula (2):

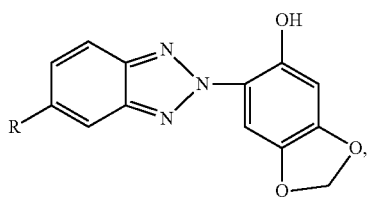

(2)

wherein R is a hydrogen atom, an alkyl group comprising 1 to 8 carbon atoms, an alkoxy group having 1 to 8 carbon atoms, a hydroxyl group, a carboxyl group, an alkyloxycarbonyl group comprising 1 to 8 carbon atoms in the alkyl group, a hydroxyalkyl group comprising 1 to 8 carbon atoms, or an alkylcarbonyloxyalkyl group comprising 1 to 8 carbon atoms in each of the alkyl groups.

4. The composition of claim 1, further comprising, per 100 parts by mass of the polycarbonate resin (A):
from 0.01 to 0.2 parts by mass of a third ultraviolet absorber (B3) having a maximum absorption wavelength of less than 360 nm in an absorption curve determined according to JIS K 7105 using the following formula

[an absorbance of the polycarbonate resin (A) comprising 0.005% by mass of the third ultraviolet absorber (B3)]– [an absorbance of the polycarbonate resin (A)].

5. The composition of claim 4, wherein the third ultraviolet absorber (B3) is at least one selected from the group consisting of a benzotriazole ultraviolet absorber lacking a sesamol group, a triazine ultraviolet absorber, a malonate ester ultraviolet absorber, and a benzoxazine ultraviolet absorber.

6. The composition of claim 1, wherein a transmittance measured according to JIS K 7105 at a wavelength of 420 nm on a 2 mm-thick molded article is not greater than 25%.

7. A molded article, comprising the polycarbonate resin composition of claim 1.

8. The composition of claim 1, wherein X in the first ultraviolet absorber (B1) is Cl.

9. The composition of claim 1, wherein X in the first ultraviolet absorber (B1) is not Cl.

10. The composition of claim 1, wherein X in the first ultraviolet absorber (B1) is Br.

11. The composition of claim 1, wherein the stabilizer (C) comprises a phosphorus stabilizer.

12. The composition of claim 1, wherein the stabilizer (C) comprises a phenolic stabilizer.

13. The composition of claim 1, wherein the stabilizer (C) comprises a sulfur stabilizer.

14. The composition of claim 1, wherein the stabilizer (C) comprises a compound of formula (C4)

(C4)

wherein $R^1$, $R^2$, and $R^3$ are independently an aryl group comprising 6 to 30 carbon atoms.

15. The composition of claim 1, wherein the stabilizer (C) comprises a compound of formula (C5)

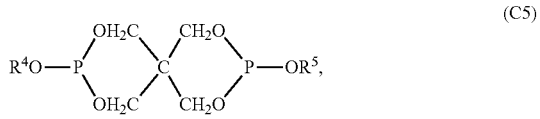

(C5)

wherein $R^4$ and $R^5$ are independently an aryl group comprising 6 to 30 carbon atoms.

16. The composition of claim 3, wherein R in the ultraviolet absorber (B2) is not methyl.

17. The composition of claim 1, wherein the stabilizer (C) comprises a pentaerythritol diphosphite.

18. The composition of claim 1, wherein the stabilizer (C) comprises a bis(2,4-di-tert-butyl-4-methylphenyl) pentaerythritol diphosphite, bis(2,6-di-tert-butyl-4-methylphenyl) pentaerythritol diphosphite, and/or bis(2,4-dicumylphenyl) pentaerythritol diphosphite.

19. The composition of claim 1, wherein the stabilizer (C) is present in a range of from 0.08 to 0.5 parts by mass.

* * * * *